(12) United States Patent
Brookhart et al.

(10) Patent No.: US 9,174,893 B2
(45) Date of Patent: Nov. 3, 2015

(54) SYNTHESIS OF PARA-XYLENE AND TOLUENE

(71) Applicant: The University of North Carolina at Chapel Hill, Chapel Hill, NC (US)

(72) Inventors: Maurice Brookhart, Carrboro, NC (US); Michael Findlater, Chapel Hill, NC (US); Damien Guironnet, Charlotte, NC (US); Thomas Warren Lyons, Carrboro, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 108 days.

(21) Appl. No.: 13/875,610

(22) Filed: May 2, 2013

(65) Prior Publication Data

US 2013/0237732 A1 Sep. 12, 2013

Related U.S. Application Data (63) Continuation-in-part of application No. PCT/US2011/058538, filed on Oct. 31, 2011.

(60) Provisional application No. 61/409,328, filed on Nov. 2, 2010.

(51) Int. Cl.
| | |
|---|---|
| *C07C 2/52* | (2006.01) |
| *C07C 5/333* | (2006.01) |
| *C07C 2/72* | (2006.01) |
| *C07C 5/32* | (2006.01) |
| *C07C 5/42* | (2006.01) |
| *C07C 5/52* | (2006.01) |

(52) U.S. Cl.
CPC ... *C07C 2/72* (2013.01); *C07C 2/52* (2013.01); *C07C 5/321* (2013.01); *C07C 5/42* (2013.01); *C07C 5/52* (2013.01); *C07C 2101/16* (2013.01); *C07C 2531/22* (2013.01)

(58) Field of Classification Search
USPC .......... 585/319, 430, 616, 530, 366
See application file for complete search history.

(56) References Cited

U.S. PATENT DOCUMENTS

| | | | | |
|---|---|---|---|---|
| 3,192,278 | A * | 6/1965 | Hastings et al. | 585/431 |
| 3,405,194 | A | 10/1968 | Iwamoto et al. | |
| 3,825,503 | A * | 7/1974 | Patrick et al. | 502/304 |
| 3,849,510 | A * | 11/1974 | Maspero et al. | 585/616 |

FOREIGN PATENT DOCUMENTS

| | | | |
|---|---|---|---|
| JP | 9-268135 | * | 10/1997 |
| RU | 1527842 | * | 10/1995 |
| WO | WO 92/19575 | | 11/1992 |

OTHER PUBLICATIONS

English abstract of JP-9-268135.*
English abstract of SU 1527842.*
International Search Report and Written Opinion, PCT/US2011/058538, mailed May 16, 2012.

* cited by examiner

*Primary Examiner* — Thuan D Dang
(74) *Attorney, Agent, or Firm* — Myers Bigel Sibley & Sajovec, P.A.

(57) ABSTRACT

A method of making para-xylene or toluene is carried out by: (a) reacting a C5 or C6 linear monoene (itself, or formed from a C5 or C6 linear alkane) with a hydrogen acceptor in the presence of a hydrogen transfer catalyst to produce a C5 or C6 diene; (b) reacting the C5-C6 diene with ethylene to produce a cyclohexene having 1 or 2 methyl groups substituted thereon; and then (c) either (i) dehydrogenating the cyclohexene in the presence of a hydrogen acceptor with a hydrogen transfer catalyst to produce a compound selected from the group consisting of para-xylene and toluene, or (ii) dehydrogenating the cyclohexene in the absence of a hydrogen acceptor with a dehydrogenation catalyst, to produce para-xylene or toluene.

20 Claims, 1 Drawing Sheet

Figure 1. 1-hexene disproportionation profile with 1 (Eq. 1)

Figure 2. Product distribution at equilibrium from disproportionation of 1-hexene with 1.

SYNTHESIS OF PARA-XYLENE AND TOLUENE

RELATED APPLICATIONS

This application is a continuation-in-part of PCT Application No. PCT/US2011/058538, filed Oct. 31, 2011, which in turn claims the benefit of U.S. Provisional Patent Application Ser. No. 61/409,328, filed Nov. 2, 2010; and also claims the benefit of U.S. Provisional Patent Application Ser. No. 61/651,690, filed May 25, 2012, the disclosures of all of which are incorporated by reference herein in their entirety.

GOVERNMENT SUPPORT

This invention was made with Government support under Grant No. CHE-0650456 from the National Science Foundation. The US Government has certain rights to this invention.

BACKGROUND OF THE INVENTION

Para-xylene remains a key intermediate in the chemical industry. Current production methods focus on catalytic reforming and cracking of non-renewable feedstocks, such as crude oil. Hence there is a need for new approaches to the formation of para-xylene (and toluene as well), preferably using feedstocks obtained from bio-renewable resources.

SUMMARY OF THE INVENTION

The present invention provides a method of making para-xylene or toluene by:

(a) reacting a C5 or C6 linear monoene with a hydrogen acceptor in the presence of a hydrogen transfer catalyst to produce a C5 or C6 diene (preferably a conjugated linear diene);

(b) reacting the C5-C6 diene with ethylene in a Diels-Alder reaction to produce a cyclohexene having 1 or 2 methyl groups substituted thereon; and then (c) either (i) dehydrogenating the cyclohexene in the presence of a hydrogen acceptor with a hydrogen transfer catalyst to produce a compound selected from the group consisting of para-xylene and toluene, or (ii) dehydrogenating the cyclohexene in the absence of a hydrogen acceptor with a dehydrogenation catalyst to produce a compound selected from the group consisting of para-xylene and toluene.

The various steps may be carried out together or separately, depending upon the arrangement most convenient for the plant layout.

In some embodiments, para-xylene is produced from ethylene as the starting material.

In some embodiments, when either 1-hexene or 1-pentene is added to the reaction it is rapidly isomerized to an equilibrium mixture of monoenes before being dehydrogenated. The most stable isomers are the internal monoenes (2-enes or 3-enes for the C6 and 2-enes for the C5). So, the methods can be started with any C6 or C5 monoene. (e.g., if internal monoenes are less expensive or more readily available).

The present invention is explained in greater detail in the specification set forth below. Applicants specifically intend that the disclosures of all US Patent references cited herein be incorporated by reference herein in their entirety.

DETAILED DESCRIPTION OF EMBODIMENTS OF THE INVENTION

"Ethylene" as used herein refers to the compound $CH_2CH_2$.

"Hydrogen acceptor" as used herein can be any suitable hydrogen acceptor, generally an organic compound containing at least one carbon-carbon double bond. Examples include, but are not limited to, C2 to C20 alkylenes such as ethylene, propylene, butylene, tent-butyl ethylene, or the C5 or C6 linear monoene itself.

"Monoene" as used herein generally refers to C5 to C6 linear alkenes containing one double bond; in other words, pentene ($C_5H_{10}$) and hexene ($C_6H_{12}$). Examples include 1-pentene, 2-pentene (cis or trans), 1-hexene, 2-hexene (cis or trans) and 3-hexene (cis or trans). Thus monoenes can be represented, in some embodiments, by Formula I, Ia, or Ib:

where R is H or $CH_3$.

"Diene" as used herein generally refers to C5 to C6 linear alkenes containing two double bonds, which double bonds are preferably conjugated (and in the case of hexadiene, both preferably internal). Examples include 1,3-pentadiene and 2,4-hexadiene. In some embodiments, both double bonds in the hexadiene are preferably both trans. Thus dienes as used herein may be represented by the Formula II:

where R is H or $CH_3$.

1. Hydrogen transfer catalysts. Hydrogen transfer catalysts useful for carrying out the present invention are known and include iridium, platinum, nickel and palladium catalysts. Examples include but are not limited to those described in U.S. Pat. Nos. 5,744,667; 5,585,530; 5,461,182; 5,227,552 and 3,321,545. Other examples of platinum, rhodium and ruthenium catalysts supported on zeolites and alumina are set forth in R. G. Pellet, *Journal of Catalysis* 177, 40-52 (1998); and S. Naito and M. Tanimoto, *J. Mol. Catal. A: Chemical* 141, 205-214 (1999).

Other examples are iridium catalysts, including but not limited to those described in U.S. Pat. No. 5,780,701; and in:

Goettker-Schnetmann, I., White, P., Brookhart, M., "Iridium Bis(Phosphinite)p-xPCP Pincer Complexes: Highly Active Catalysts for the Transfer Dehydrogenation of Alkanes" *J. Am, Chem. Soc.* 2004, 126, 1804-1811;. Crabtree, R. H.; Mellea, M. F.; Mihelcic, J. M.; Quirk, J. M. "Alkane dehydrogenation by iridium complexes" *J. Am. Chem. Soc.* 1982, 104, 107-13; Felkin, H.; Fillebeen-Khan, T.; Holmes-Smith, R.; Lin, Y. "Activation of carbon-hydrogen bonds in saturated hydrocarbons. The selective, catalytic functionalization of methyl groups by means of a soluble iridium polyhydride system" *Tetrahedron Lett.* 1985, 26, 1999-2000; Burk, M. J.; Crabtree, R. H. "Selective catalytic dehydrogenation of alkanes to alkenes" *J. Am. Chem. Soc.* 1987, 109, 8025-32; Maguire, J. A.; Goldman, A. S. "Efficient Low-Temperature Thermal Functionalization of Alkanes. Transfer-Dehydrogenation Catalyzed by Rh(PMe$_3$)$_2$(CO)Cl in Solution Under High Pressure Dihydrogen Atmosphere" *J. Am. Chem. Soc.* 1991, 113, 6706-6708; Maguire, J. A.; Petrillo, A.; Goldman, A. S. "Efficient Transfer-Dehydrogenation of Alkanes Catalyzed by Rhodium Trimethylphosphine Complexes Under Dihydrogen Atmosphere" *J. Am. Chem. Soc.* 1992, 114, 9492-9498; Gupta, M.; Hagen, C.; Flesher, R. J.; Kaska, W. C.; Jensen, C. M. "A highly active alkane dehydrogenation catalyst: stabilization of dihydrido Rh and Ir complexes by a P-C-P pincer ligand" *Chem. Commun.* 1996, 2083-2084; Wang, K.; Goldman, M. E.; Emge, T. J.; Goldman, A. S. "Transfer-Dehydrogenation of Alkanes Catalyzed by Rhodium(I) Phosphine Complexes" *J. Organomet. Chem.* 1996, 518, 55-68; Gupta, M.; Hagen, C.; Kaska, W. C.; Cramer, R. E.; Jensen, C. M. "Catalytic Dehydrogenation of Cycloalkanes to Arenes by a Dihydrido Iridium P-C-P Pincer Complex" *J. Am. Chem. Soc.* 1997, 119, 840-841; Gupta, M.; Kaska, W. C.; Jensen, C. M. "Catalytic Dehydrogenation of Ethylbenzene and THF by a Dihydrido Iridium P-C-P Pincer Complex" *Chem. Commun.* 1997, 461-462; Xu, W.; Rosini, G. P.; Gupta, M.; Jensen, C. M.; Kaska, W. C.; Krogh-Jespersen, K.; Goldman, A. S. "Thermochemical Alkane Dehydrogenation Catalyzed in Solution Without the Use of a Hydrogen Acceptor" *Chem. Commun.* 1997, 2273-2274; Liu, F.; Pak, E. B.; Singh, B.; Jensen, C. M.; Goldman, A. S. "Dehydrogenation of n-Alkanes Catalyzed by Iridium "Pincer" Complexes. Regioselective Formation of Alpha-Olefins" *J. Am. Chem. Soc.* 1999, 121, 4086-4087; Liu, F.; Goldman, A. S. "Efficient thermochemical alkane dehydrogenation and isomerization catalyzed by an iridium pincer complex" *Chem. Commun.* 1999, 655-656; Jensen, C. M. "Iridium PCP pincer complexes: highly active and robust catalysts for novel homogeneous aliphatic dehydrogenations" *Chem. Commun.* 1999, 2443-2449; Krogh-Jespersen, K.; Czerw, M.; Summa, N.; Renkema, K. B.; Achord, P. D.; Goldman, A. S. "On the Mechanism of (PCP)Ir-catalyzed Acceptorless Dehydrogenation of Alkanes: a Combined Computational and Experimental Study" *J. Am. Chem. Soc.* 2002, 124, 11404-11416; and Zhu, K.; Achord, P. D.; Zhang, X.; Krogh-Jespersen, K.; Goldman, A. S. "Highly Effective Pincer-Ligated Iridium Catalysts for Alkane Dehydrogenation. DFT Calculations of Relevant Thermodynamic, Kinetic, and Spectroscopic Properties" *J. Am. Chem. Soc.* 2004, 126, 13044-13053.

In one embodiment, the hydrogen transfer catalyst is an iridium pincer complex catalyst, such as described above, and also described in U.S. Pat. No. 6,982,305 to Nagy. Examples of such catalysts include but are not limited to compounds of Formula X, Y, X', or Y':

wherein:
each R is independently H or a C$_1$-C$_{30}$ hydrocarbyl radical;
each R$_1$ is independently a C$_1$-C$_{30}$ hydrocarbyl radical; and
each X is independently selected from O and CH$_2$.
each olefin is an unsubstituted, mono-, di-, tri-, or tetra-substituted linear or cyclic alkene containing compound.

2. Reactions and Conditions.

C5 or C6 linear monoene feedstocks such as pentene and hexene can be produced in accordance with known techniques. In some embodiments, the hexene feedstock is produced from ethylene in accordance with known techniques, which ethylene is in turn produced from ethanol in accordance with known techniques, which ethanol is in turn produced by fermentation of biorenewable materials in accordance with known techniques. Hence, the present invention provides, in some embodiments, a biological source for paraxylene.

The C5 or C6 linear monoene is reacted with a hydrogen acceptor in the presence of a hydrogen transfer catalyst to produce a C5 or C6 linear diene, preferably a conjugated diene (for example, 1,3-pentadiene or 2,4-hexadiene). Any suitable hydrogen acceptor may be employed, such as the C5 or C6 linear monoene itself (which must then be supplied in an excess amount), ethylene or propylene (which can then be easily cracked back from the alkane to alkene form), etc. Suitable hydrogen transfer catalysts are described above. In some embodiments, the diene is hexadiene which is preferentially produced as compared to the corresponding hexatriene: for example, is produced at a molar ratio of hexadiene to hexatriene of at least 10:1, 20:1, 50:1, 100:1, 200:1, 400:1 or more. The reaction is, in some embodiments, carried out at a temperature of from 100, 200 or 250 degrees Centigrade to 500 or 600 degrees Centigrade, and is carried out at a pressure of from 100, 200, or 500 psi to 5,000 or 7,000 psi.

A linear diene produced as described above (preferably with both double bonds in the trans orientation) can be reacted with ethylene in a Diels-Alder reaction to produce a cyclohexene having 1 or 2 methyl groups substituted thereon. Specific reaction conditions are not critical. The Diels-Alder cycloaddition reaction step can be carried out in accordance with known techniques or variations thereof that will be apparent to those skilled in the art. See, e.g., Diels, O. and Alder, K, Synthesen in der hydroaromatischen Reihe, *Justus Liebig's Annalen der Chemie* 460: 98 (1928); see also U.S. Pat. Nos. 4,053,528; 4,419,497; 4,538,013; 7,662,996; 7,691,159; 7,704,912; and 7,786,201. In some embodiments, this reaction is carried out as a one-pot reaction in the same reaction vessel as the monene dehydrogenation reaction described above. In some embodiments, this reaction is carried out with the same catalyst as the monoene dehydrogenation reaction described above. In some embodiments, ethylene is used as both the hydrogen acceptor in the monene dehydrogenation reaction described above and as the dienophile in the Diels-Alder reaction. The cyclohexene so produced may thus be described as a compound of Formula III:

(III)

wherein R is H or $CH_3$.

The C6 cycloalkene (e.g., of Formula III) can be dehydrogenated in accordance with known techniques (see, e.g., U.S. Pat. No. 4,221,678 to Ishikawa) typically in the presence of any suitable hydrogen acceptor (e.g., ethylene, propylene), to produce a compound of Formula IV:

(IV)

wherein R is H (toluene) or $CH_3$ (p-xylene). In some embodiments, this reaction is carried out with a hydrogen transfer catalyst that is the same as that used to dehydrogenate the monoene in the reaction described above. Hence in some embodiments this reaction is also carried out as a one-pot reaction in the same reaction vessel as one or both of the reactions described above.

In some embodiments, the cyclohexene is dehydrogenated in the absence of a hydrogen acceptor with a dehydrogenation catalyst to produce a compound selected from the group consisting of para-xylene and toluene. Such dehydrogenation can be carried out in accordance with known techniques, or variations thereof that will be apparent to those skilled in the art. See, e.g., Borade, R. B.; Zhang, B.; Clearfield, A. "Selective dehydrogenation of cyclohexene to benzene using Pd-exchanged α-zirconium phosphate" *Cat. Lett.* 1997, 45, 233-235; El Kady, F. Y. A.; Shaban, S. A.; Abo El Naga, A. O. "Catalytic dehydrogenation of cyclohexene over $MoO_3/\gamma-Al_2O_3$" *Transition Met. Chem.* 2011, 36, 237-244.; Tsai, M. C.; Friend, C. M.; Muetterties, E. L. "Dehydrogenation Processes on Nickel and Platinum Surfaces. Conversion of Cyclohexane, Cyclohexene, and Cyclohexadiene to Benzene" *J. Am. Chem. Soc.* 1982, 104, 2539-2543. B. C. Gates, J. R. Katzer, and G. C. A.; Schuit, eds., *Chemistry of Catalytic Processes* (McGraw-Hill, New York, 1979). De Miguel, S. R.; Castro, A. A.; Scelza, O. A. "Effect of the addition of alkali metals on the metallic phase of $Pt/Al_2O_3$ catalysts." *Cat. Lett.* 1995, 32, 281-291.

3. Utility. p-Xylene is useful as (among other things) a feedstock in the production of terephthalic acid and dimethyl terephthalate, both monomers used in the production of polyethylene terephthalate (PET) plastic bottles and polyester clothing.

Toluene is useful as (among other things) a common solvent for paints, paint thinners, silicone sealants, chemical reactants, rubber, printing ink, adhesives, lacquers, etc. and as a feedstock for the production of toluene diisocyanate (which is in turn useful for the manufacture of polyurethane foam), etc.

The present invention is explained in greater detail in the following non-limiting Examples.

EXAMPLE 1

Selective Formation of 2,4-hexadiene

In an argon-filled glovebox, $(^{iPr4}\text{Anthraphos})\text{Ir}(C_2H_4)$ (3.0 mg, 0.005 mmol) was dissolved in n-hexane (e.g. hexane: 0.182 ml, 1.44 mmol); 1-hexene (4 equiv with respect to n-hexane, 0.691 ml, 5.76 mmol) and mesitylene (0.079 mL, internal standard) were then added to the solution.

The total solution (n-hexane, 1-hexene and mesitylene) volume was 0.95 mL. The contents were heated in a preheated oil bath at 165° C. At regular intervals, the reaction mixture was brought to room temperature, cooled by means of an ice-bath and an aliquot of the sample analyzed by GC in comparison with authentic products. The assignments of the major products were confirmed with GC-MS and are set forth in Table 1 below.

TABLE 1

| | $(^{iPr4}\text{Anthraphos})\text{Ir}(C_2H_4)$ | | | | | |
|---|---|---|---|---|---|---|
| Time (h) | 3-Hexene-trans (mM) | Hexane (mM) | Benzene (mM) | Monoenes (mM) | Hexadiene-cis (mM) | Hexadiene-trans (mM) |
| 2 | 1686 | 1382 | 0 | 180 | 388 | 550 |
| 5 | 1053 | 1989 | 0 | 151 | 287 | 413 |
| 12 | 649 | 1980 | 0 | 150 | 380 | 533 |
| 24 | 608 | 2146 | 0 | 96 | 388 | 550 |
| 48 | 550 | 2267 | 0 | 91 | 400 | 566 |

EXAMPLE 2

Selective Formation of 2,4-hexadiene from Neat 1-hexene

In an argon-filled glovebox, $(^{iPr4}\text{Anthraphos})\text{Ir}(C_2H_4)$ (8.0 mg, 0.0127 mmol) was dissolved in 1-hexene (2.5 g, 29.7 mol) and sealed with a Teflon stopcock. The solution was then heated in a preheated oil bath and 180° C. At regular intervals, the reaction mixture was brought to room temperature and an aliquot of the sample analyzed by GC. An aliquot of 90 μL of solution was combined with 10 μL of mesitylene as an internal standard. The sample solution was then analyzed by GC with comparison to authentic products. The relative amounts of the products are shown below in TABLE 2.

TABLE 2

| Entry | Time (min) | Hexanes (%) | Hexenes (%) | Hexadienes (%) | Benzene (%) |
|---|---|---|---|---|---|
| 1 | 0 | 100 | 0 | 0 | 0 |
| 2 | 30 | 2.09 | 70.85 | 14.57 | 0.03 |
| 3 | 90 | 20.63 | 59.10 | 20.2 | 0.07 |
| 4 | 150 | 30.58 | 39.48 | 39.7 | 0.12 |
| 5 | 210 | 33.99 | 32.05 | 33.77 | 0.19 |

EXAMPLE 3

Diels Alder Reaction of Hexadiene Product Mixture

The crude reaction mixture from EXAMPLE 2 above was separated from the ($^{iPr4}$Anthraphos)Ir($C_2H_4$) catalyst by vacuum transfer. 1.5 g of the resulting solution was placed into a high-pressure reactor with a total volume of 8 mL. The reactor was then pressurized to 500psi with ethylene and left to stir at room temperature for 30 min. Once the solution was saturated with ethylene, the pressure vessel was pressurized again to 500 psi, sealed and heated to 250° C. for 48 hours.

Upon completion, the pressure vessel was cooled to room temperature and the contents removed. 1.36 g of solution were recovered and analyzed by GC. 95% conversion of 2,4-trans, trans-hexadiene to 3,6-dimethylcyclohexene was observed by GC with <1% conversion of 2,4-trans, cis-hexadiene or 2,4-cis, cis-hexadiene.

EXAMPLE 4

Transfer Dehydrogenation of Diels Alder Adduct to p-xylene

The crude product mixture from EXAMPLE 3 above was dried over molecular sieves (4 Å) and degassed by freeze-pump-thaw techniques. In an argon filled glovebox 0.200 mL of this solution, 2 mg of ($^{iPr4}$POCCP)Ir($C_2H_4$), (0.0037 mmol, 3 mol % relative to 3,6-dimethylcyclohexene) and 17.2 μL of mesitylene as internal standard were added to a 1 mL thick-walled glass flask equipped with a Teflon screw top. The sealed flask was removed from the glovebox and placed in an oil bath preheated at 180° C. At regular intervals, the reaction mixture was brought to room temperature and an aliquot of the sample analyzed by GC. After 5 days, 20% conversion of 3,6-dimethylcyclohexene was observed with 7% yield of p-xylene.

EXAMPLE 5

Synthesis of p-Xylene from Ethylene

With diminishing oil reserves, the production of commodity chemicals will increasingly rely on alternative feedstocks. In this regard, new routes to para-xylene (para-dimethylbenzene, PX) are of particular interest as PX is one of the highest volume chemical intermediates derived from petroleum. (H. A. Wittcoff, et al., Plotkin Industrial Organic Chemicals (John Wiley & Sons, Inc., 2004) pp. 329). The primary use of PX is for the production of the dimethyl ester of terephthalic acid, which is copolymerized with ethylene glycol to produce polyethylene terephthalate polyester (PET). The 11 billion pounds of PET consumed annually in the US (as of 2007) (B. Kuczenski, R. Geyer, Resour. Conserv. Recycl. 54 1161-1169 (2010)) are used to manufacture a wide variety of common products including plastic bottles, polyester fibers and films such as MYLAR® film, PX is produced by catalytic reforming of various crude oil streams, which results in a mixture of benzene, toluene, and the ortho, meta and para xylene isomers (so-called BTX). For synthesis of PET, high purity PX is required and thus several technologies have been developed to purify and maximize PX yields. The remarkably close boiling points of the xylene isomers (ortho, meta, para: 138.5, 139.1, 144.0° C.) makes distillation an unappealing separation method. Low temperature crystallization and surface adsorption are often used, taking advantage of the difference in melting points of the three isomers (ortho, meta, para: −25.0, −47.4, 13.2° C.). (Speight, J. G. Chemical Process and Design Handbook (McGraw-Hill, New York, 2002) pp. 2557-2560). In order to increase the yield of PX from these sources, technologies have been developed to generate xylenes via toluene disproportionation and/or xylene isomerization over zeolite catalysts. The most widely used of these catalysts is ZSM-5, which catalyzes the transalkylation and isomerization of xylenes. In addition to the costly separations and purifications required, the fraction of xylenes from crude oil is highly dependent on the reforming stream. The content of xylenes may vary as much as 12-33% by volume of the reformate depending on the source, catalyst, and reforming conditions, (Speight, J. G. Chemical Process and Design Handbook (McGraw-Hill, New York, 2002) pp. 2557-2560). While recent, significant progress has been made in developing new isomerization (W. Yuan, et al., J. Am. Chem. Soc. 126, 4776-4777 (2004), J. Breen et. al., J. Am. Chem. Soc. 127, 5020-5021 (2005)) and separation technologies (Vermoortele, F. et al. J. Am. Chem. Soc. 133, 18526-18529 (2011), M. Lusi, L. J. Barbour, Angew. Chem. Int. Ed. 51, 3928-3931 (2012)) a direct, selective route to PX from petroleum sources has yet to be developed.

Alternative approaches to xylenes have involved a variety of strategies utilizing both biomass and petroleum feedstocks. For example, 2,5-dimethylfuran, derived from carbohydrates will undergo a Diels-Alder reaction and subsequent dehydration to produce PX. (T. A. Brandvold. U.S. Pat. No. 0,331,568 A1 (2010), C. L. Williams et al. ACS Cat. 2, 935-939 (2012), K. Takanishi and S. Sone, PCT Application WO 2009110402). The concurrent production of unwanted side products however, has prevented this method from being more broadly utilized. A more selective reaction was achieved by Toste, who has shown 2,5-dimethylfuran will undergo a Sc(OTf)$_3$-catalyzed Diels-Alder reaction with acrolein at −60° C. to provide an adduct which can be converted to PX following oxidation, dehydration and decarboxylation steps. While selective, the low temperature requirement renders this PX synthesis poorly suited for a larger scale industrial process. (M. Shiramizu, F. Toste, *Chem. Eur. J.* 17, 12452-12457 (2011)). Recently, Virent has made PX from hydrocarbons produced from plant sugars via its BioForming process. (Virent Makes Xylene, Gasoline From Plants, Chemical and Engineering News Jun. 13, 2011, R. Cortright, P. Blommel U.S. Pat. 7,977,517). This technology, however, still relies on reforming hydrocarbons and produces the normal mix of ortho, meta and para isomers, requiring separation and purification as outlined above. Another route to xylenes developed collaboratively by the Goldman and Brookhart groups (R. Ahuja et al., Nat. Chem. 3, 167-171 (2011)) involves transfer dehydrogenation of linear alkanes to aromatics. This dehydroaromatization approach however, yields only OX (together with ethyl benzene) from octane.

In this report we describe the synthesis of PX using ethylene as the sole feedstock. The route is highly selective and produces no OX or MX isomers as by-products. Ethylene is an attractive raw material for two reasons. First, it can be readily derived from ethanol and is therefore biorenewable. Braskem, in Brazil, has already commercialized this process producing 200,000 tons of polyethylene a year from ethylene derived from sugar cane. (Braskem press release. September, 24, 2010). Second, and perhaps most significant, the vast reserves of natural gas in the Marcelleus shale deposits (shale gas) contain substantial fractions of ethane which is readily cracked to ethylene. It is generally agreed that ethylene derived from shale gas will become a major (non-petroleum based) source of this feedstock in the near future. (Dow press release. April, 21, 2012). To that end, several petrochemical firms have announced their intention to increase U.S. ethylene production, including Shell's proposed ethane cracker in western Pennsylvania. (D. Gilbert, "Chemical Makers Ride Gas Boom" Wall Street Journal, 19, Apr., 2012: B1 Print, Chevron Phillips press release. Apr. 30, 2012, L. Bewley "Petrochemicals: shale gas restores U.S. competitiveness." Chemical Week 26 Mar. 2012)).

1305 (2004)). Catalytic disproportionation of 1-hexene via transfer dehydrogenation with another equivalent of substrate yields hexadiene and hexane. Subsequent Diels-Alder reaction of 2,4-hexadiene (2,4-HXD) with ethylene affords 3,6-dimethylcyclohexene, which, upon dehydrogenation, produces PX and hydrogen. Significantly, this synthetic route produces only PX, uncontaminated by the OX and MX isomers. Details of the development and optimization of this process are described below.

2,4-Hexadiene Synthesis. We began our studies by exploring the conversion of 1-hexene to hexadienes. Previous work had shown catalytic transfer dehydrogenation of n-alkanes n>5 with iridium pincer complexes using four equivalents of the sacrificial alkene acceptor TBE (tert-butylethylene) ultimately resulted in formation of cyclic aromatic products. Aromatics are produced via formation of linear, conjugated trienes followed by ring closure to cyclohexadienes and further transfer dehydrogenation to the aromatic. We expected that the disproportionation of hexene (in which one equivalent of hexene acts as the acceptor for dehydrogenation of a second equivalent of hexene) may be terminated at the diene stage prior to benzene formation. This expectation was based

Scheme 1. Synthesis of PX from ethylene

Our initial strategy for implementing the synthesis of PX from ethylene is outlined in Scheme 1. 1-Hexene can be produced via chromium-catalyzed trimerization of ethylene, a commercial process for preparing this monene. (J. Freeman et al., U.S. Pat. No. 5,856,257; A. Carter et al., Chem. Commun. 858-859 (2002); D. F. Wass, PCT Patent WO 2002004119; T. Agapie et al., J. Am. Chem. Soc. 126, 1304- on the fact that olefin and diene isomerizations are fast relative to dehydrogenation and thus the major diene isomers produced from hexene should be 2,4-hexadienes (2,4-HXDs). These dienes cannot undergo transfer dehydrogenation; further dehydrogenation can only occur from the thermodynamically much less favored 1,3-diene isomers.

Scheme 2. Catalysts screened for hexene disproportionation (Eq. 1)

Scheme 2 shows four iridium pincer catalysts that were screened for disproportionation of 1-hexene into hexadienes and hexane. A 0.04 mol % catalyst loading was used and the degassed hexene solution was heated in a closed, glass vessel at 180° C. for 3.5 h. Conversions were monitored by gas chromatography. The turnover frequencies (TOFs) shown were calculated based on 30 min conversions and the turnover numbers (TONs) were based on product formation after 3.5 h. Surprisingly, the more hindered t-butyl-substituted catalysts, 3 (A. S. Goldman et al. Science. 312, 257-261 (2006)) and 4 (J. Choi et al. J. Am. Chem. Soc. 131, 15627-15629 (2009)), exhibited almost no activity in contrast to the remarkably high activity these complexes display in transfer dehydrogenation of cyclooctane using TBE as an acceptor. The less hindered isopropyl-substituted systems, 1 (P. Romero et al., *Organometallics*, 27, 3422-3429 (2008)) and 2, showed good activities, with the anthraphos-based system, 1, exhibiting a TOF and TON of ca. four times that of 2. Further experiments with 1 at a lower catalyst loading (0.01 mol %) showed a TOF of 677 $h^{-1}$; a total TON of 7477 was achieved when the catalyst was recycled three times. These experiments demonstrate the exceptional stability of the anthraphos pincer complex.

Figure 1:
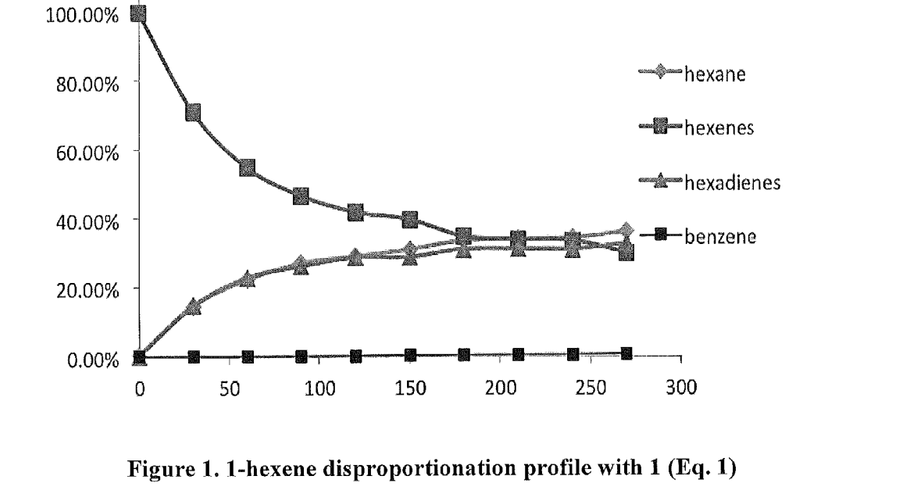
FIG. 1. 1-hexene disproportionation profile with 1 (Eq. 1).
Figure 2:
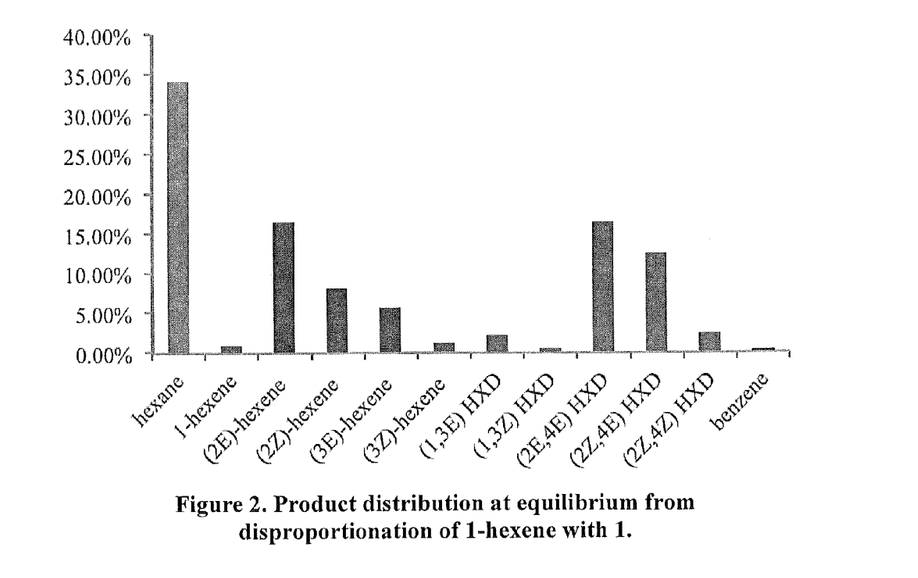
FIG. 2. Product distribution at equilibrium from disproportionation of 1-hexene with 1.

The kinetic profile of 1-hexene disproportionation catalyzed by 1 (0.04 mol %, 180° C.) was followed by GC and is displayed in FIG. 1. The iridium pincer complex, 1, catalyzes isomerization of hexenes and hexadienes much faster than transfer hydrogenation under these conditions, thus 1-hexene is rapidly converted to a thermodynamic mixture of hexenes prior to significant hydrogen transfer and the hexadienes produced appear as the thermodynamic ratio of dienes. As is evident from FIG. 1, the reaction reaches equilibrium at ca. 3.5 h under these conditions with a $K_{eq} \approx 1$. The thermodynamic ratios of the hexene and hexadiene isomers are illustrated in FIG. 2 which shows the full product distribution at equilibrium.

Diels-Alder Reaction. Next, conditions for the desired Diels-Alder reaction with ethylene were explored. Literature reports suggested that the cycloaddition reaction of pure (2E, 4E)-HXD with ethylene required high temperatures and pressures (185° C., 4300 psi) for the cycloaddition to occur. The 2E,4Z and 2Z,4Z isomers were unreactive under these conditions. (P. Bartlett, K. Schueller *J. Am. Chem. Soc.* 90, 6071-6077 (1968)). We were able to achieve high conversion of (2E,4E)-HXD (96%) and (1,3) HXD (100%) in the crude reaction mixture to Diels-Alder products after 48 h at 600 psi and 250° C. Under these conditions selective formation of the Diels-Alder adduct with (2E, 4E)-HXD is observed, with minimal conversion of the (2E, 4Z) and (2Z, 4Z) HXD isomers. As shown by results summarized in Table 3, only the concentration of the two reactive dienes has changed significantly to produce A and B, illustrating the high selectivity observed in this reaction. Additionally, the GC trace for this reaction only shows one peak for isomer A with no other peak that could be assigned as the other stereoisomer.

TABLE 3

Product distribution from Diels-Alder reaction

| | hexane | hexenes | (1,3E)-HXD | (1,3Z)-HXD | (2E,4E)-HXD | (2E,4Z)-HXD | (2Z,4Z)-HXD | A | B |
|---|---|---|---|---|---|---|---|---|---|
| Start (mmol) | 33.9% | 34.8% | 1.6% | 0.3% | 15.1% | 11.7% | 2.3% | 0 | 0 |
| Final (mmol) | 31.4% | 31.1% | 0 | 0 | 0.6% | 7.5% | 1.7% | 23.9% | 2.9% |

*Numbers shown are in mol % of total solution

Dehydrogenation. In the final step of the synthesis of PX we sought to dehydrogenate 3,6-dimethylcyclohexene, the Diels-Alder adduct. The overall reaction shown in Eq. 1 involves loss of two equivalents of $H_2$ and formation of a stable aromatic structure.

(2)

The high positive entropy offsets the positive enthalpy (Δ H=+21 kcal/mol) and renders the reaction highly exergonic at temperatures above 200° C., suggesting this dehydrogenation can be accomplished "acceptorless" with a heterogeneous catalyst. (Calculated for 3,6-dimethylcyclohexene) Indeed, dehydrogenation of cyclohexene to benzene over heterogeneous catalysts has ample literature precedent (M. Tsai et al., *J. Am. Chem. Soc.* 104, 2539-2543 (1982); R. Borade et al., *Cat. Lett.* 45, 233-235 (1997), M. Aramenía et al. *J. Mol Cat. A.* 151, 261-269 (2000)). In this study, commercial catalysts Pd/C, Pt/C, and Pt/Al$_2$O$_3$ were screened. Crude reaction mixtures of the Diels-Alder adducts were passed in the vapor phase using nitrogen as carrier gas over a bed of these catalysts at 300-500° C. and the product mixtures trapped and analyzed by GC. In initial screening, all these catalysts gave good conversion (>80%) of the starting Diels-Alder adduct to PX. Upon further optimization, Pt/Al$_2$O$_3$ at 400° C. was observed to give the highest yield (93%) of PX. Ethylbenzene (EB) was also observed in high yield from this reaction (88%) with a final ratio of 8.5:1, PX:EB (Scheme 3). Importantly, EB is another valuable aromatic as it is a precursor to styrene.

Scheme 3. Dehydrogenation with Pt/Al$_2$O$_3$

Thus far, a step-wise approach to PX using ethylene as the sole feedstock has been outlined. The efficiency and utility of this sequence could be improved if ethylene were to serve as the hydrogen acceptor for 1-hexene dehydrogenation and drive conversion of hexene to higher yields of hexadienes. Heating 1-hexene at 250° C. with 600 psi of ethylene for 24 hours in the presence of 0.32 mol % 1 resulted in conversion of 1-hexene into HXD (35.1% HXD, Table 4, entry 2). Significantly, the dienes produced underwent a subsequent Diels-Alder reaction with ethylene in situ, providing the 3,6-dimethylcyclohexene (16.9% A, entry 2) in one pot. This remarkable result demonstrates a significant step forward in this approach to PX. The yield of HXD (and ultimately PX) is no longer limited by the equilibrium disproportionation of 1-hexene into HXD and hexane, making this one pot approach to 3,6-dimethylcyclohexene a more attractive route for PX synthesis from ethylene. Further heating of the reaction vessel resulted in nearly complete conversion with respect to hexenes (7.9% remained in solution after 192 hours, entry 7). Only trace amounts of hexane are observed, indicating ethylene has served as the dominant acceptor. The selective conversion of 1-hexene to A and B also suggests that the unreactive HXD's are isomerized to reactive HXD's under these reaction conditions. Thus a high conversion to A and B is observed for the Diels-Alder reaction with minimal HXD remaining. Additionally, the Diels-Alder adducts are further dehydrogenated under these reaction conditions resulting in 3.2% PX and 2.9% EB as well as partially dehydrogenated A and B (Table 4, Other). Importantly, the partially dehydrogenated species (Table 4, Other) can easily be dehydrogenated to aromatics via the Pt-catalyzed dehydrogenation.

TABLE 4

Product distribution from one-pot HXD formation, Diels Alder reaction

| Entry | Time (h) | Hexane | Hexenes | HXDs | Benzene | A | B | PX | EB | Other |
|---|---|---|---|---|---|---|---|---|---|---|
| 1 | 0 | | 100% | | | | | | | |
| 2 | 24 | 0.4% | 42.1% | 35.1% | 1.5% | 16.2% | 4.7% | | | |
| 3 | 48 | 0.6% | 30.4% | 23.5% | 3.6% | 33.4% | 6.7% | 0.8% | 1.0% | |
| 4 | 72 | 0.5% | 24.6% | 14.9% | 4.5% | 44.6% | 8.3% | 1.2% | 1.4% | |

TABLE 4-continued

| 5 | 96 | 0.5% | 21.6% | 10.4% | 4.8% | 48.7% | 8.8% | 1.4% | 1.6% | 2.2% |
| 6 | 144 | 0.4% | 14.2% | 2.0% | 5.3% | 59.7% | 10.2% | 2.3% | 2.1% | 3.8% |
| 7 | 192 | 0.2% | 7.5% | 0.2% | 4.0% | 65.5% | 12.2% | 3.2% | 2.9% | 4.3% |

In summary, we have demonstrated a new and selective route to PX using ethylene as the sole feedstock. The route features an iridium-catalyzed disproportionation of 1-hexene (derived from trimerization of ethylene) to hexane and hexadienes. The 2E,4E-HXD generated undergoes Diels-Alder cycloaddition with ethylene to form 3,6-dimethylcyclohexene which can be quantitatively dehydrogenated over a heterogeneous Pt catalyst to yield PX and hydrogen. High yields of HXDs can be formed and the Diels-Alder reaction can be done in a one-pot process by using ethylene as the hydrogen acceptor.

Materials and Methods

General Considerations. All manipulations were carried out under an argon atmosphere using an argon filled glove box or using standard Schlenk techniques. 1-Hexene was purchased from Aldrich and distilled over Na prior to use. Ethylene (99.95% polymer purity) was purchased from Airgas National Welders and used as received. ($^{iPr4}$anthraphos)Ir($C_2H_4$) was synthesized according to known methods (R. Ahuja et al., *Nat. Chem.* 3, 167-171 (2011)). Gas chromatographic analysis of reactions was conducted on an Agilent Technologies 6850 GC instrument fitted with a fused silica capillary column (100 m length×0.25 mm ID×0.50 μm film thickness with the following method.

FID detector: Temp=300° C.
Initial Temperature: 40° C.
Final Temperature: 250° C.
Oven Program: 40° C., hold for 20 min
Ramp 1: 85° C./min to 150° C., hold for 5 min Ramp 2: 10° C./min to 250° C., hold for 20 min Products were confirmed using authentic samples and calibrated with an internal standard (mesitylene).

Typical procedure for iridium catalyzed disproportionation of 1-hexene. In an argon filled glovebox ($^{iPr4}$Anthraphos)Ir($C_2H_4$) (8.5 mg, 0.0135 mmol) was dissolved in 1-hexene (2.5 g, 29.7 mmol) in a 4 mL Kontes vial equipped with a Teflon screw-cap, sealed and added to an oil bath at 180° C. At regular intervals, the reaction mixture was brought to room temperature and an aliquot of the sample analyzed by GC. An aliquot of 90 μL of solution was combined with 10 μL of mesitylene as an internal standard.

Scale up procedure for iridium catalyzed disproportionation of 1-hexene. In an argon filled glovebox a 20 mL Kontes vial equipped with a Teflon screw-cap was filled with ($^{iPr4}$Anthraphos)Ir($C_2H_4$) (10.7 mg, 0.017 mmol) and dissolved in 1-hexene (10.0 g, 118.8 mmol) sealed and added to an oil bath at 180° C. The reaction was monitored by GC analysis. When equilibrium had been reached the solution was cooled to room temperature and the volatiles separated from the iridium catalyst via vacuum transfer. To measure a maximum TON the remaining iridium catalyst was recharged with 1-hexene and the procedure repeated until the catalyst was recycled a total of three times.

Procedure for the Diels Alder reaction of hexadienes mixture with ethylene. In a 22 mL stainless steel Parr reactor was added 5.0 g of crude solution isolated by vacuum transfer from the disproportionation. The vessel was sealed, then pressurized with ethylene to 600 psi and left at room temperature for 30 minutes in order for ethylene to dissolve into solution. Once saturated, the vessel was sealed at a static pressure of 600 psi and heated to 250° C. for 48 hours. Upon completion the reaction was cooled to room temperature and the contents of the vessel collected in a tared vial. An aliquot of this reaction mixture was taken and combined with a standard (mesitylene) and analyzed by GC. 4.89 g isolated after reaction. Some contents were lost due to the volatility of C6 hydrocarbons. 95% conversion was observed with respect to (2E, 4E)—hexadiene.

Procedure for the dehydrogenation of Diels-Alder adduct mixture. A Carbolite furnace with a quartz tube was filled with 1% Pt/$Al_2O_3$ (25 g). To one end of the furnace tube was attached a glass trap with an oil bubbler. The other end was fitted with 14/20 ground glass joint and connected to a two-neck 50 mL round bottom flask. The second neck of the rbf was fitted with a septum and $N_2$ was added to the system via a needle through this septum. The furnace was warmed to 400° C. under an atmosphere of $N_2$ for 30 minutes to dry the catalyst. Following this preactivation, the glass collection trap was cooled with liquid $N_2$ and 2.0 mL of DA mixture added to the two neck rbf. $N_2$ was bubbled through the solution at such a rate so that the oil bubbler emitted a bubble once per second. Once the reaction began, the two-neck rbf was slowly warmed to 70° C. to ensure all the material was carried over the catalyst. When the reaction was complete (~1 hr) the contents of the trap were warmed and collected by washing with pentanes. Standard (mesitylene) was added and the solution analyzed by GC.

Procedure for one-pot HXD formation, Diels-Alder reaction. In an argon filled glovebox a 22 mL stainless steel Parr reactor was charged with (iPr4Anthraphos)Ir($C_2H_4$) (24.2 mg, 0.038 mmol) and dissolved in a mixture of 1-hexene (1.5 mL, 12.0 mmol) and mesitylene (1.5 mL, 10.8 mmol). The vessel was sealed, taken out of the glovebox, then pressurized with ethylene to 600 psi and left at room temperature for 30 minutes in order for ethylene to dissolve into solution. At 24 hour intervals the vessel was cooled to room temperature, and as aliquot removed for GC analysis. To do this, the vessel was depressurized, brought into an argon filled glovebox and an aliquot removed via syringe. The vessel was then recharged with ethylene as described above and heated to 250° C.

Computational Details. All calculations were performed using a Gaussian 09 program (Frisch et al., Gaussian 09, Revision B.01, Gaussian, Inc., Wallingford, Conn., 2009) on a Linux cluster. The restricted wave function was used for the singlet ground state. The free energies are evaluated by B3LYP functional (A Becke, *Phys. Rev. A* 1988, 38, 3098-3100; A. Becke, *J. Chem. Phys.* 1993, 98, 5648-5652; C. Lee et al., *Phys. Rev. B* 1988, 37, 785-789) with triple-ζ 6-311G (d) basis set on all atoms following the geometry optimizations at the same level in the gas phase. In addition, compound methods G2 (L. Curtiss et al., *J. Chem. Phys.* 1991, 94, 7221-7230) and CBS-QB3 (J. Ochterski et al., *J. Chem. Phys.* 1996, 104, 2598-2619; J. Montgomery et al., *J. Chem. Phys.* 1999, 110, 2822-2827) were also used. Frequency calculations on the optimized structures confirmed the local minimum with no imaginary frequencies found.

The thermochemistry of cyclohexene dehydrogenation to benzene was calculated to calibrate the computational method. The G2 method showed minimal errors from the experimental data and was thus used in calculations for cis-3,6-dimethylcyclohexene dehydrogenation to p-xylene.

The foregoing is illustrative of the present invention, and is not to be construed as limiting thereof. The invention is defined by the following claims, with equivalents of the claims to be included therein.

That which is claimed is:

1. A method of making a compound, comprising:
   (a) reacting a C5 or C6 linear monoene with a hydrogen acceptor in the presence of a hydrogen transfer catalyst to produce a C5 or C6 conjugated linear diene; and
   (b) reacting said C5-C6 conjugated linear diene with ethylene in a Diels-Alder reaction to produce a cyclohexene having 1 or 2 methyl groups substituted thereon,
   wherein said reacting steps (a) and (b) are
   (i) carried out as a one-pot reaction in the same reaction vessel; or
   (ii) carried out with the same catalyst.

2. The method of claim 1, wherein said reacting step (a) further comprises:
   reacting a C5 or C6 linear alkane with a hydrogen acceptor in the presence of a hydrogen transfer catalyst to product said C5 or C6 linear monoene.

3. The method of claim 1, wherein said hydrogen transfer catalyst is an iridium, platinum, palladium or nickel hydrogen transfer catalyst.

4. The method of claim 1, wherein said hydrogen transfer catalyst is an iridium pincer complex catalyst.

5. The method of claim 1, wherein said C5 or C6 linear diene is selected from the group consisting of 1,3-pentadiene and 2,4-hexadiene.

6. The method of claim 1, and wherein said diene is hexadiene and is produced at a molar ratio of hexadiene to hexatriene of at least 10:1.

7. The method of claim 1, wherein said hydrogen acceptor is a C2-C20 alkylene.

8. The method of claim 7, wherein said hydrogen acceptor is ethylene, propylene, butylene, tert-butylethylene, or said C5 or C6 linear monoene.

9. The method of claim 8, wherein said hydrogen acceptor is ethylene.

10. The method of claim 1, wherein said reacting step (a) is carried out at a temperature of from 100 degrees Centigrade to 600 degrees Centigrade, and at pressure of from 100 psi to 7,000 psi.

11. The method of claim 1, wherein said reacting steps (a) and (b) are carried out as a one-pot reaction in the same reaction vessel.

12. The method of claim 1, wherein said reacting steps (a) and (b) are carried out with the same catalyst.

13. The method of claim 1, further comprising the step of:
   (c) dehydrogenating said cyclohexene in the presence of a hydrogen acceptor with a hydrogenation catalyst to produce a compound selected from the group consisting of para-xylene and toluene; or
   dehydrogenating said cyclohexene in the absence of a hydrogen acceptor with a dehydrogenation catalyst to produce a compound selected from the group consisting of para-xylene and toluene, and optionally with ethyl benzene produced concurrently therewith.

14. The method of claim 13, wherein said hydrogen acceptor is ethylene, and wherein para-xylene and ethyl benzene are concurrently produced.

15. The method of claim 13, wherein said reacting steps (a), (b) and (c) are carried out as a one-pot reaction in the same reaction vessel.

16. The method of claim 13, wherein said reacting steps (a) and (c) are carried out with the same catalyst.

17. The method of claim 1, wherein said C5-C6 linear monoene is a compound of Formula I:

where R is H or CH$_3$.

18. The method of claim 1, wherein said C5-C6 linear diene is a compound of Formula II:

where R is H or CH$_3$.

19. The method of claim 1, wherein said cyclohexene is a compound of Formula III:

wherein R is H or CH$_3$.

20. The method of claim 1, wherein said C5 or C6 linear monoene is 1-hexene, and wherein said 1-hexene is produced by trimerizing ethylene in the presence of a chromium catalyst.

* * * * *